United States Patent [19]

Wagner et al.

[11] Patent Number: 4,857,512

[45] Date of Patent: Aug. 15, 1989

[54] IMMUNOSTIMULATING POLYSACCHARIDES, METHOD FOR USING SUCH, AND PHARMACEUTICAL PREPARATIONS CONTAINING THEM

[75] Inventors: Hildebert Wagner, Breitbrunn; Meinhart H. Zenk, Munich; Holger Ott, Emmerthal, all of Fed. Rep. of Germany

[73] Assignee: Lomapharm, Rudolf Lohmann GmbH KG, Pharmazeutische Fabrik, Langes Feld, Fed. Rep. of Germany

[21] Appl. No.: 933,482

[22] Filed: Nov. 21, 1986

[30] Foreign Application Priority Data

Nov. 27, 1985 [DE] Fed. Rep. of Germany ....... 3541945

[51] Int. Cl.$^4$ .................... A61K 31/715; A61K 31/70
[52] U.S. Cl. ..................... 514/54; 536/123; 536/128; 514/885; 424/195.1
[58] Field of Search ............... 424/195.1; 514/54, 885; 536/123, 128

[56] References Cited

U.S. PATENT DOCUMENTS 3,418,311 12/1968 Sakai et al. ............... 536/123
4,511,559 4/1985 Szendrei et al. ............ 536/128
4,614,733 9/1986 Yoshikumi et al. .......... 536/123

FOREIGN PATENT DOCUMENTS 2721014 11/1978 Fed. Rep. of Germany ... 424/195.1
3042491  7/1982 Fed. Rep. of Germany ........ 514/54
40-24791 10/1965 Japan .................... 514/54
43-16048  7/1968 Japan .................... 514/54
50-34094 11/1975 Japan .................... 514/54
58-34803  3/1983 Japan .................... 536/123
82/03771 11/1982 World Int. Prop. O. ........... 514/54

OTHER PUBLICATIONS

Wagner et al; Chemical Abstracts, vol. 97: 44198c (1981).
Stickl et al; Chemical Abstracts, vol. 100: 8906d (1983).
Wagner et al; Chemical Abstracts, vol. 98: 166802m (1981).
Wagner et al; Chemical Abstracts, vol. 101: 143766u (1984).
Stimpel et al; Infection and Immunity, 46(3): 845–849 (Dec. 1984).

Primary Examiner—Ronald W. Griffin
Assistant Examiner—Nancy S. Carson
Attorney, Agent, or Firm—Ratner & Prestia

[57] ABSTRACT

The present invention pertains to plant polysaccharides acting on the immune system and a process for isolating the polysaccharides from plant cell cultures. The purified polysaccharides can be used as drugs, specifically as immunomodulators or immune mediators, in animal medicine.

11 Claims, 1 Drawing Sheet

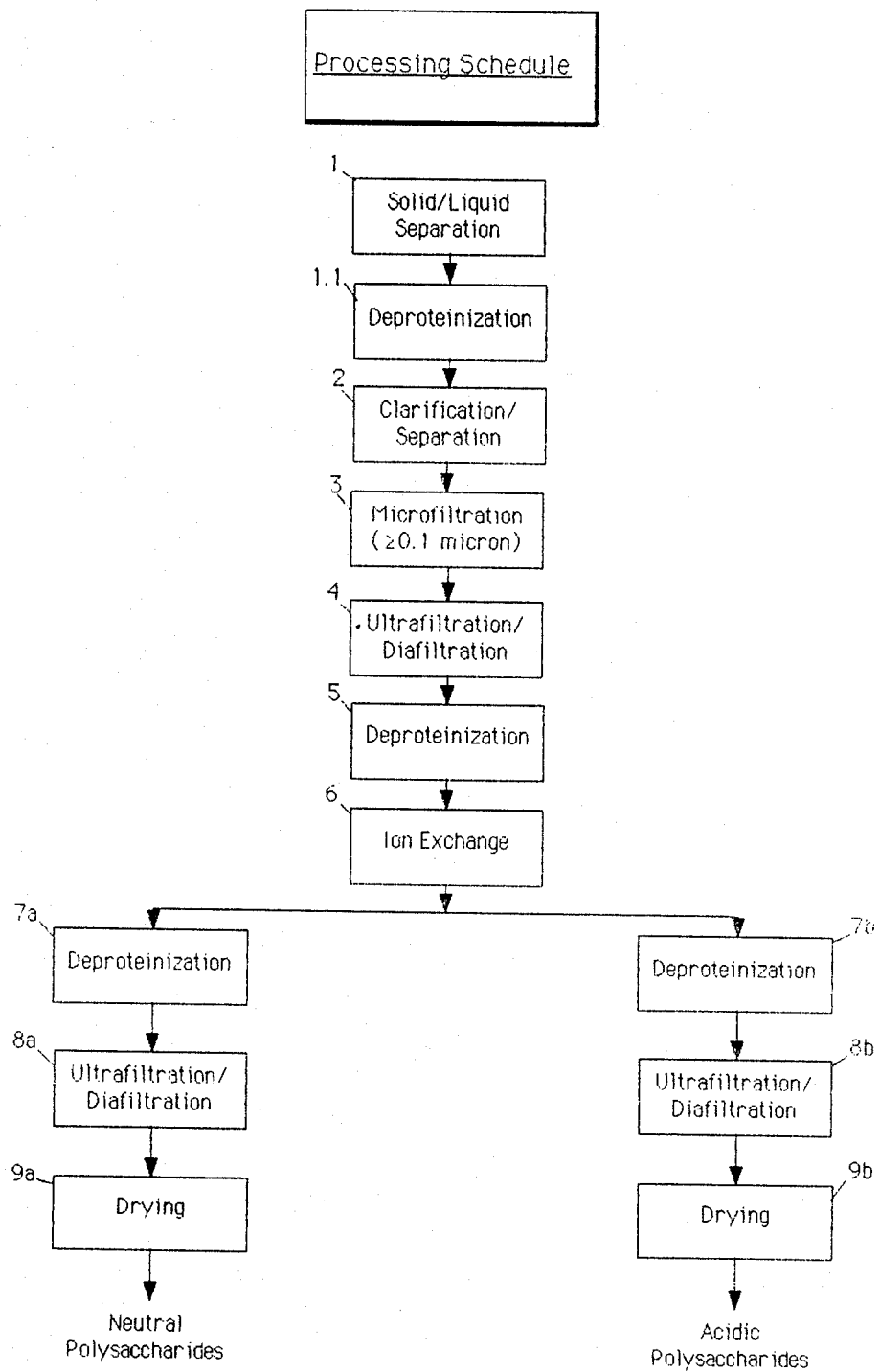

IMMUNOSTIMULATING POLYSACCHARIDES, METHOD FOR USING SUCH, AND PHARMACEUTICAL PREPARATIONS CONTAINING THEM

BRIEF DESCRIPTION OF THE INVENTION

The present invention pertains to new polysaccharides with immunostimulating action from *Echinacea purpurea* (Linné) Moench and *Echinacea angustifolia* (De Vandolle) cell cultures, to a process for preparing them, as well as to drugs containing the said polysaccharides.

BACKGROUND OF THE INVENTION

Immunostimulation as a therapeutic concept has long been known in medicine. In general, it is defined as the injection of substances which themselves have only weak if any antigenic effect, but are nevertheless able to induce the body's own defense mechanisms in a nonspecific or even specific manner. According to the data currently available, a great number of substances are able to stimulate immune defense, and especially various minerals, e.g., Al(OH)$_3$, MgSO$_4$, beryllium, vegetable oils with or without added mycobacteria, as well as a number of constituents of plants can be mentioned among them. The substance class of the lectins should be mentioned in this connection in particular; their immunostimulating effect was investigated intensively. The lectins (phytohemagglutins) are plant proteins or glycoproteins. Polysaccharides are other plant constituents with immunostimulating effect which were isolated from lower and higher fungi, lichens and algae, and investigated. The entire complex subject of immunostimulation was described in detail e.g., by Chedid, L. et al. in *Immunstimulation* [Immunostimulation], Springer Verlag, Heidelberg, New York, 1980; Heidelberger, M.: Structure and Immunological Specificity of Polysacc[h]arides, *Fortschritte d. Chem. org. Naturst.*, Vol. 42, pp. 288 (1982); and Drews, H.: Possibilities of Immunostimulation, *Swiss Pharma*, 2, 9 (49) (1980).

In most known cases it has been impossible to definitely clarify the exact mode of action of the immunostimulating substances. Among other things, these substances generally influence the proliferation of the immunocompetent cells, but they do not leave behind any memory reaction. This means that the primary targets of the action of the immunostimulating substances are the macrophages and granulocytes, as well as the T and B lymphocytes. The effect of the immunostimulants may be direct or indirect, e.g., via the complement system or the lymphocytes, via the production of interferon or lysosomal enzymes (e.g., lymphokines, colony-stimulating factor and others), as well as via an increase in macrophagocytosis and microphagocytosis. Cascade effects and simultaneous influences on a plurality of defense mechanisms are always to be expected because of the entanglement of nonspecific and specific defense mechanisms.

The preferred applications of immunostimulation in medicine are primarily the therapy of mixed infections and chronic, persistent, chemotherapy-resistant bacterial and viral infections, the prevention of opportunistic infections in patients at risk, the therapy of malignant diseases and, to a certain extent, also the treatment of autoimmune diseases. Immunostimulants can also be used in cytostatic therapy for partial compensation of the immunosuppression associated with such therapy.

A number of extraction methods have been described in the literature for isolating polysaccharides from starting materials of vegetable origin: Whistler, R. L. and J. L. Sannella: *Methods in Carbohydrate Chemistry*, editors: Whistler, R. L. and J. N. Bemiller, Vol. V, pp. 34–36, Academic Press, New York 1965; Tomoda, M., K. Shimada, Y. Saizo, and M. Sugi: *Chem. Pharm. Bull.*, Vol. 28, No. 10, p. 2933 (1980).

Thus, depending on the type of polysaccharide, the plant material in question is extracted with cold or hot water, aqueous salt solutions, dilute acids or alkalies, or dimethyl sulfoxide. From the solutions thus obtained, the crude polysaccharide fraction is obtained, in general, by precipitation with alcohol, via complexing with heavy metal salts or quaternary ammonium salts. The crude polysaccharide fractions are then separated by ion exchange chromatography, gel filtration chromatography and bioaffinity chromatography.

The following disadvantages are inevitably associated with the isolation of polysaccharides from native starting plant materials according to the known methods. The lipophilic accompanying substances, e.g., chlorophyll, which are also obtained during the extraction, are difficult to separate, or they can be separated only after lengthy extraction with organic solvents. Depending on the nature of the native starting plant material, the crude polysaccharide fractions prepared are always obtained in both qualitatively and quantitatively different compositions by the various purifications of the same plant material. Another major disadvantage is the fact that it is absolutely necessary to use alkaline or acidic extractants, which are inevitable in the isolation of special polysaccharide types. The primary, secondary or tertiary structures of the polysaccharides are altered, and the immunostimulating effect is therefore influenced by the use of these extractants.

The object of the present invention is to present processes for isolating polysaccharides from higher plants which are free from the aforementioned disadvantages and permit simple and efficient preparation of polysaccharides from higher plants.

Another object of the present invention is to propose pharmaceutical formulations which contain the immunostimulating agents for use in human therapy.

BRIEF DESCRIPTION OF THE FIGURE

The FIGURE depicts a schematic flow for an industrial-scale process for making the polysaccharides of the present invention.

TABLE OF ABBREVIATIONS

Araf—Arabinofuranoside
Fuc—Fucose
Ga—Galactose
GalA—Galacturonic Acid
Galp—Galactopyranoside
Glc—Glucose
Rha—Rhamnose
Xyl—Xylose

DETAILED DESCRIPTION OF THE INVENTION

According to the present invention, plant cell cultures are used as the starting material; the particular advantages of the use of cell cultures lies primarily in the fact that the desired products are always obtained in the same chemical composition and yield. In addition, if cell cultures are used, the above-mentioned lipophilic accompanying substances are not obtained, or they are obtained in a very small percentage only. Another advantage of cultures is the fact that the desired polysaccharides are released directly into the culture medium surrounding the cells, so that the further purification may be carried out in a relatively simple manner. This is based on the unusual ability of the plant cells to release large quantities of polysaccharides into the culture medium.

Another advantage of the process according to the present invention is that the polysaccharide isolation time is reduced and the treatment of the starting material with extractants, some of which exert an undesirable effect, is avoided, so that artifact formation of the desired products in connection with the processing can be eliminated for the most part.

In general, the process for isolating the polysaccharides of this invention comprises incubating any part of one of the plants Echinacea purpurea (Linné) Moench or Echinacea angustifolia (De Vandolle) to form callus on a nutrient medium, forming a suspension culture starting with the callus cells and removing from that suspension, after separation of the cellular material, suspended material having a molecular weight more than $5 \times 10^3$ daltons. This may be accomplished, for example, by repeated precipitation, with ethanol (or alternatively with acetone, ammonium sulfate, cetyltrimethyl ammonium bromide, $CaCl_2$, Fehling's solution, etc)., and centrifugation. Preferably, the separation process includes deproteinizing the separated material, such as by treatment with trichloroacetic acid and subsequently with sodium acetate. Preferably also the separation process includes purification of the separated material by dialysis and lyophilization.

A process for preparing plant cell cultures from Echinacea purpurea and subsequently a process for isolating immunostimulating polysaccharides from these cell cultures will be described below as examples.

Sterile seedlings, leaf, flower, stalk or root parts of Echinacea purpurea or Echinacea angustifolia stands, which are first induced to form callus on solid culture medium, are used as the starting material for preparing the cell cultures.

To do so, seedlings, leaf, flower, stalk and root parts of Echinacea purpurea are implanted in agar-containing Linsmaier-Skoog medium (Linsmaier, E. M. and F. Skoog: Physiol. Plant., Vol. 18, p. 100 (1965)), and the medium is incubated for 14 to 28 days at 24° C., adding auxins, e.g., 2,4-dichlorophenoxyacetic acid. The auxins may be varied qualitatively. As was described in the Handbook of Plant Culture (editors: David A. Evans, William R. Sharp, Philipp V. Ammirato and Aysuyuki Yamada, Vol. 1, Macmillan Publishing Co. A Division of Macmillan Inc., New York), it is also possible to use other culture media to prepare callus and cell cultures.

After the first callus has formed, after approximately 14 days, it is transferred into a liquid culture medium. These cell cultures are suspension cultures; they are filled into 1-liter or 1.5-liter Erlenmeyer flasks containing about 250 or 1000 ml liquid culture medium, respectively, and the flasks are shaken at 100 rpm. After incubation for approximately 14 days at 22°-28° C., the suspension culture is filtered off, the cellular residue is lyophilized to determine its weight, and the culture medium filtered off is subjected to further processing.

(A) Isolation of the Polysaccharides from the Cell Culture Medium

Unless specified otherwise, all the procedures described below were carried out at 4°-8° C.

(a) Isolation of the Crude Polysaccharide Fraction

The cells and cellular components of a total of 20 liters of cell suspension cultures are filtered off, and the residue is washed with 5 liters of distilled water.

The cellular residue is deep-frozen and lyophilized to determine its weight. Approximately 270 g of lyophilized cell material is thus obtained. In portions of 3 liters each, the combined filtrates (20 liters) are mixed with three times their volume of ethanol (95%). The precipitates formed overnight are separated from the supernatant solutions first by cautious decanting, and then by centrifugal separation (10,000 rpm/30 minutes). The combined centrifugates are dissolved in 4 liters of distilled water, slowly mixed with 15% trichloroacetic acid to a final concentration of 7.5% while cooling with ice, and separated by centrifugation after 1 hour. The gel-like precipitate is discarded; the clear supernatant is divided into portions and is precipitated with 3 times its volume of ethanol (95%). The precipitates formed are separated by centrifugation after 12 hours, combined, and taken up in 1/20 of the volume of sodium acetate solution (2%) originally used. The solution is stirred for 8 hours at 4° C., and then filtered. The filtrate is now mixed with an equal volume of ethanol (95%), allowed to stand for 12 hours, the precipitate formed is separated by centrifugation, taken up in 1/10 its volume of distilled water, dialyzed against demineralized water for 2 days, and then lyophilized (1:1 precipitate).

The supernatant of the 1:1 precipitate with ethanol is mixed with 1.5 times its volume of ethanol (95%) and allowed to stand for 48 hours. The precipitate is then separated by centrifugation, dissolved in distilled water, dialyzed for 48 hours, and freeze-dried. The following yields are obtained: 1:1 precipitate: 2 g, ca. 1% relative to the freeze dried cell components. 1:4 precipitate: 1 g, ca. 0.5% relative to the freeze-dried cell components.

Freeze-dried cell residue: 270 g.

(b) A shorter process, with the trichloroacetic acid precipitation omitted, will be described below for isolating the crude polysaccharide fraction.

The cellular components of a total of 10 liters of cell suspension culture are filtered off, and the residue is washed with distilled water. The cellular residues are again lyophilized to determine their weight (about 120 g lyophilized cell material), and the combined filtrates are mixed in portions with three times their volume of ethanol (95%). The precipitates formed are separated from the supernatant solutions first by cautious decanting, and then by centrifugation (10,000 rpm, 30 minutes). The combined centrifugates are dissolved in distilled water, insoluble components are separated by centrifugation (10,000 rpm, 30 minutes), and the supernatant solution is mixed with an equal volume of ethanol (95%). The precipitates formed are separated by centrifugation after 12 hours, after which the centrifugate is dissolved in distilled water, the solution is dialyzed against demineralized water for 48 hours, and then lyophilized. The supernatant of the 1:1 precipitate is mixed with 1.5 times its volume of ethanol (95%), the precipitate formed is separated by centrifugation after 48 hours (10,000 rpm, 30 minutes), then dissolved in distilled water, dialyzed against demineralized water for 48 hours, and then lyophilized (1:4 precipitate).

The following yields are obtained:
1:1 precipitate: 1.5 g, ca. 1.2%, relative to the lyophilized cell material.
1:4 precipitate: 0.7 g, ca. 0.5%, relative to the lyophilized cell material.
Lyophilized cell residue: 120 g.

(B) Isolation of a Neutral Polysaccharide A and Three Other Polysaccharides (B - D) from the 1:1 Precipitate (a) Preliminary Separation An anion exchange column, e.g., a DEAE-Sepharose ® CL-6 B column in the acetate form, is changed with an aqueous solution of the 1:1 precipitate. A neutral polysaccharide A with positive optical rotation is obtained in the aqueous eluate. The elution of the acidic polysaccharide fractions is carried out by an NaCl gradient of 0–0.75M.

A polysaccharide (B) with negative optical activity is obtained at an NaCl concentration of about 0.2M, and two other dextrorotatory polysaccharide fractions (C, D) are obtained at a salt concentration of about 0.4M.

(b) Purification of the Neutral Polysaccharide A by Anion Exchange chromatography and Gel Filtration To separate acidic polysaccharide portions still present, the polysaccharide fraction A obtained in Example (a) is first subjected to anion exchange chromatography e.g., through DEAE-Sepharose ® CL-6 B and DEAE-Trisacryl ® M. Both columns are eluted with $H_2O$. The neutral fraction A purified in this manner is then subjected to further purification by gel filtration on Sephacryl ® S 400. This makes it possible to separate low-molecular-weight, optically inactive components from dextrorotatory polysaccharide. The purified polysaccharide A is tested for homogeneity, and its molecular weight is determined.

The following yield is obtained: ca. 0.07% (relative to 100 g lyophilized cell material)

(C) Isolation of the Polysaccharides E and F from the 1:4 Precipitate (a) Preliminary Searation A polysaccharide (E) with positive optical rotation is obtained in the aqueous eluate by anion exchange chromatography on DEAE-Sepharose ® CL-6 B. An acidic polysaccharide with negative rotation (polysaccharide F) is obtained after elution at an NaCl concentration of approximately 0.2M.

(b) Purification of the Polysaccharide Fractions E and F

Polysaccharide E is purified by gel filtration, e.g., on Ultrogel ® AcA with a 0.2M NaCl solution as the eluant. The polysaccharide E is found in the exclusion volume of the column, and the low-molecular-weight accompanying substances without optical activity in the fractionating zone or in the entire volume. The acidic polysaccharide fraction F is subjected to a second anion exchange chromatography, e.g., on DEAE-Trisacryl ® M. If pure water is used for the elution, only small traces will be found in the eluate. The polysaccharide F is eluted as a relatively symmetrical peak at an NaCl concentration of 0.2M. Both polysaccharides are subsequently subjected to further gel filtration on Sephacryl ® S400 using a 0.2M NaCl solution as the eluant.

The following yields are obtained: polysaccharide E 0.18%
polysaccharide F 0.14%, (both relative to 100 g lyophilized cell material)

(D) Industrial-Scale Process for Isolating the Neutral and Acidic Polysaccharides According to the FIGURE 1. After the cell suspension has been separated into the cellular residue and the cell-free culture medium by filtration or centrifugation and the cellular residue discarded, the cell-free culture medium, which usually accounts for about 75 to 85 wt. % of the original suspension volume, can be deproteinized even now as described below under 5 (step 1.1.). This step can be omitted here, but it must be carried out in step 5.

2. Residual turbidity due to cell fragments or precipitated protein is eliminated by clarification in a flow-through separator, preferably in a chamber separator or disk separator, and the solids separated are discarded. This step can be omitted if the deproteinization was not carried out already in step 1.1.

3. Colloidally dissolved components as well as high-molecular-weight compounds (molecular weights $>10^6$ Dalton) are removed by microfiltration (step 3). Polysulfone membranes in tubular or capillary modules with a pore size $\geq 0.1$ micron are preferably used. It is also possible to use ultra filtration membranes with separation limits of $>10^5$ Dalton as an alternative here.

4. To achieve high product yields, the retentate is subjected to diafiltration with demineralize water when a predetermined minimum volume is reached. The permeate and the diafiltrate are purified, and the retentate is discarded.

The combined permeates are first concentrated by ultrafiltration (concentration factors between 10 and 500, depending on the initial volume and the plant size), and then they are subjected to diafiltration until a conductivity below 100 μmoh/cm is reached. The permeate is discarded.

The membranes used for the concentration should have separation limits of 10,000 Dalton or lower. Polysulfone or cellulose acetate membranes in tubular, capillary or spiral coil modules are preferably used.

As an alternative to the diafiltration, it is also possible to carry out desalting by dialysis or gel filtration.

5. Unless deproteinization was carried out in 1.1., the concentrated retentate is deproteinized. Two alternative methods can be used for this purpose:

5. 1. Heating to temperatures of 90° C. to 130° C.

5. 2. Filtration or centrifugation after cooling to separate the precipitates.

or 5. 1. Mixing the solution with trichloroacetic acid (TCA) up to a concentration of 7.5 wt. %.

5. 2. Allowing to stand at 4° C. for at least 12 hours.

5. 3. Separation of the precipitates by filtration or centrifugation.

5. 4. Dialysis of the clarified solution against demineralized water until a conductivity of <100 μmoh/cm is reached.

6. The concentrated retentate is eluted on the weak anion exchange column first with water as the eluant to isolate the neutral polysaccharide fraction (corresponding to the polysaccharide fraction A), and then with a salt gradient (sodium acetate, NaCl, etc). from 0 to 4 molar concentration to isolate the acidic polysaccharide fractions (corresponding to the polysaccharide fraction F).

7. If necessary, the individual fractions are deproteinized as described under 5.

8. The individual fractions are subjected to ultrafiltration and diafiltration as was described under 4.

9. The products are subsequently dried by lyophilization, vacuum drying, or spray drying.

The yields reached are dependent on the quality of the fermentation mixture used, and they amount to about 10 to 100 ppm for the individual fractions, depending on the original suspension volume.

(E) Structures of the Polysaccharides Isolated (a) Polysaccharides A and E

1. Molecular weight determination

The molecular weights of the polysaccharides A and E were determined by gel chromatography on Sephacryl® S 400, using water or a 0.2M NaCl solution as the eluant, as well as by high-performance liquid chromatography (HPLC).

HPLC system used:
(a) u-Porasil-Gpc-60 + u-Bondagel E 125.
(b) u-Bondagel E 125 + 5-Bondagel E 500 (Waters)

Buffer system: 0.2M or 0.5M phosphate buffer pH=6.0.

Reference substances: dextran T 10, T 40, T 70, T 110, T 500, T 2000.

A mean molecular weight of 10,000 (range: 5–15,000) was determined according to these methods for polysaccharide E, and 25,000 (range: 20–30,000) was determined for the polysaccharide A.

2. Structure:

Both polysaccharides are fucogalactoxyloglucans, which are composed of fucose, galactose, xylose and glucose at the ratio of 0.1:0.4:1:1.5.

The main chains of the polysaccharides consist of (1→4)-beta-linked glucose units, approximately 65% of which are branched at the C-6 position.

The side chains have relatively different compositions and have a maximum chain length of 3 sugar units. In the simplest case the terminal xylose is bound directly to the C-6 atom of the glucan skeleton. In addition, galactose - (1→2) - xylose, fucose - (1→2) - galactose - (1→2) - xylose and galactose - (1→2) - galactose (1→2) xylose side chains are present as well. Based on the oligosaccharides isolated, it can be assumed that the polysaccharides consist mostly of repeat units of heptasaccharides and decasaccharides.

Both polysaccharide A and the polysaccharide B are acetylated to an extent of approximately 8%.

Basic structure of the polysaccharides A and E

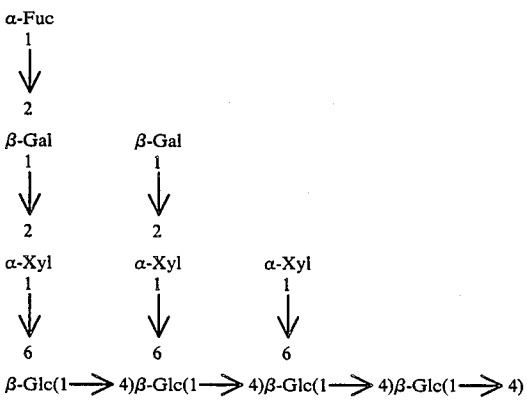

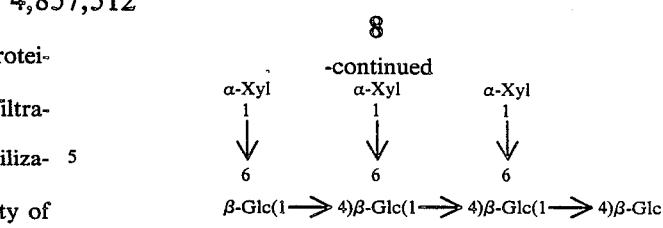

(b) Basic structure of polysaccharide F

1. As was described in Example (a), the mean molecular weight of polysaccharide F was found to be 75,000 with a range of 65,000–85,000 (0.5M phosphate buffer pH 6.0) and 110,000 with a range of 100,000–120,000 (0.2M phosphate buffer pH 6.0), depending on the buffer system used.

Polysaccharide F is an acidic arabinogalactan The basic skeleton consists of (1→3)-beta-linked galactose chains, which are linked together via a rhamnogalacturonan.

Every other galactose unit of the (1→3)-beta-galactan chain is linked with the (1→6)-beta-galactose side chains via the C-6 atom. In turn, nearly 70% of these side chains are linked with terminal arabinose in the C-3 position.

In addition to these polysaccharide components, it was also possible to find longer, more heavily branched (1→5)-alpha-arabinan chains. This arabinan moiety can be bound to the arabinogalactan moiety or to the rhamnogalacturonan.

Structure of the arabinogalactan moiety of polysaccharide F

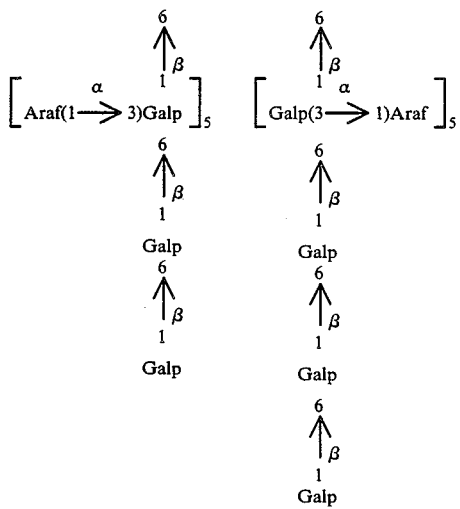

Basic structure of the rhamnogalacturonan moiety of polysaccharide F

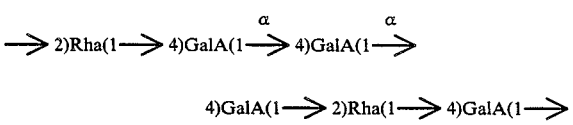

Basic structure of the arabinan moiety of polysaccharide F

-continued

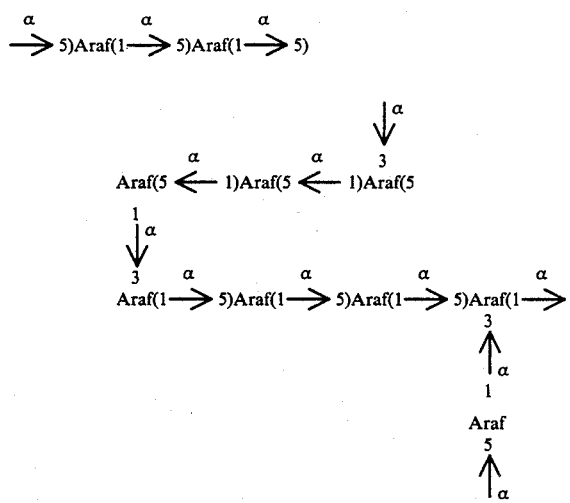

(F) Pharmacological effects of the Polysaccharides Isolated

Because no specific test methods have been available for testing the immunostimulating effects of substances, in vitro and in vivo methods which permit measurement of the influence of compounds or plant extracts on the functional status and the performance capacity of the mononuclear system, as well as stimulability of T and B lymphocytes have typically been used.

(a) Granulocyte test according to Brandt: (Brandt, L.: *Scand. J. Haematol.* (Suppl.) 2 (1967).

In this in vitro granulocyte test according to Brandt, the number of yeast cells or bacteria phagocytized by a granulocyte fraction isolated from human serum is determined under the microscope. The percentage increase in phagocytosis by certain polysaccharide fractions is measured.

TABLE 1

Percentage increase in phagocytosis by individual polysaccharide fractions in the granulocyte test according to Brandt

| Polysaccharide From the cell culture medium: | Phagocytosis values in percentage at the concentrations | | | | |
|---|---|---|---|---|---|
| | 1 | $10^{-1}$ | $10^{-2}$ | $10^{-3}$ | $10^{-4}$ | $10^{-5}$ mg/ml |
| 1:1 precipitate | — | 21.5% | 27.8% | 0% | — | — |
| 1:4 precipitate | — | 15.4% | 18.3% | 13.5% | — | — |
| PS* A | 17.6% | 21.3% | 28.1% | 20.1% | 9.3% | — |
| PS E | — | 10.8% | −4% | −1.5% | — | — |
| PS F | — | 0.6% | 3% | 10.8% | — | — |

*PS = polysaccharide (b) Another test for determining the effects of immunostimulating substances is the so-called carbon clearance method. According to this method, the rate of elimination of carbon particles from the blood of animals is measured by spectrophotometry. This rate of elimination is an indicator of the phagocytosis activity (Biozzi, G., B. Benacerraf, and B. N. Halpern: *Br. J. Exp. Pathol.*, Vol. 34, p 441 (1953)).

The influence of the polysaccharide fractions from the cell culture on the carbon clearance of mice is shown in Table 2.

TABLE 2

Influence of polysaccharide fractions from cell culture on carbon clearance on mice. Administration of one 10 mg dose of substance per kg of body weight to mice

| Polysaccharide fraction | $K_{substance}/K_{controls}$* | DSK value |
|---|---|---|
| 1:1 precipitate | 1.77 | 2 |
| PS A | 1.6 | 2 |
| PS E | 1.2 | 1 |
| PS F | 1.4 | 1 |

*The regression coefficients were corrected according to Drews, taking the liver, spleen and body weights of the mouse in question into account.

In the immunological studies, the 1:1 precipitate from the culture medium showed markedly higher phagocytosis rates in the granulocyte test than did the 1:4 precipitation product. It was possible to observe the same difference in activity in the single components isolated from the 1:1 and 1:4 precipitation products as well.

Polysaccharides A

Contrary to the polysaccharide E from the 1:4 precipitate, the polysaccharide A isolated from the 1:1 precipitate with ethanol showed markedly higher immunostimulating activity, in agreement with the granulocyte and carbon clearance tests.

Polysaccharide F

Like the other arabinogalactans tested, polysaccharide F proved to be only moderately active in the test systems used, but it did have a marked effect in the TNF (Tumor Necrosis Factor) test.

(c) Macrophage activation to direct cytotoxicity against tumor cells, determined according to Stimpl, M., A. Proksch, H. Wagner, and M. L. Lohmann-Matthes: *Infection and Immunity*, Vol. 46, p. 845 (1984).

In this test, polysaccharide A activated $2 \times 10^5$ mouse peritoneal macrophages to complete cytotoxicity against P 815 tumor cells up to a dilution of 6 to 50 microg per $2 \times 10^5$ macrophages.

The polysaccharides according to the present invention can be administered either separately as a pure substance or in the form of pharmaceutical preparations, even though the compounds are preferably administered in a combination. The drug combination is preferably in the form of a formulation which (1) contains the polysaccharides according to the present invention either alone or in combination with each other, and (2) contains one or more appropriate binders, carriers and/or further auxiliary materials, and (3) may also contain additional therapeutically active substances.

The carrier materials, binders and/or auxiliary materials must be pharmaceutically and pharmacologically tolerable, so that they can be combined with the other components of the formulation or preparation and do not exert any adverse effect on the organism treated.

The formulations include those which are suitable for oral or parenteral (including subcutaneous, intradermal, intramuscular and intravenous) administration, even though the best route of administration is dependent on the patient's status.

The formulations can be in the form of single doses. The formulations are prepared according to methods known in the field of pharmacology. All methods include the step of mixing or combining the polysaccharides according to the present invention (i.e., the active substances) with the carrier material, binder and/or auxiliary material, with the latter materials representing an additional component. In general, the formulations are prepared by intimately mixing the active substances with the liquid carrier materials or with the finely dispersed carrier materials or both and by subsequently bringing the product obtained into the desired form of administration, if necessary. The formulations according to the present invention, which are suitable for oral administration, can be in the form of discrete units, such as capsules, cachets or tablets, which contain a predetermined quantity of the active substance according to the present invention, as well as in the form of powders or granules, in the form of a solution or of a suspension in an aqueous or nonaqueous liquid, or in the form of a liquid oil-in-water emulsion or a liquid water-in-oil emulsion.

The active substances can also be in the form of a bolus or a paste.

The tablets can be prepared by pressing or molding, adding one or more of the usual auxiliary materials if necessary.

The formulations suitable for parenteral administration include sterile injection solutions in aqueous or nonaqueous media, antioxidants, buffers, bacteriostatics and dissolved substances, which render the formulation isotonic for the human body. Furthermore, the polysaccharides according to the present invention can be in the form of sterile suspensions in aqueous or nonaqueous media which may contain suspending agents and thickeners. The formulations can be in the form of single or multiple doses, e.g., in the form of ampules or tightly sealed bottles, and they can also be stored in the lyophilized form, so that if administration is required, it is only necessary to add sterile liquid carrier material, e.g., water suitable for injection purposes, immediately before use. The injection solutions and suspensions prepared immediately before the administration can be prepared from sterile powder, granules and tablets of the above-described kind.

Besides the aforementioned components, the preparations according to the present invention may also contain other components which are suitable for the formulations in question. For example, the pharmaceutical preparations to be administered orally may contain flavorings.

The appropriate quantities of active substances suitable for administration vary as a function of the particular field of therapy. In general, the active substance concentration in a single-dose formulation is 5% to 95% of the total formulation. In the case of a single-time administration, this corresponds to 1 to 50 mg per kg body weight. However, this dosage can be varied within broad limits depending on the administration form, the patient's general condition, and the field of therapy.

We claim:

1. Biochemically pure polysaccharide fractions having an average molecular weight of about 10,000 with a molecular weight range of from about 5,000 to about 15,000 of the general structure:

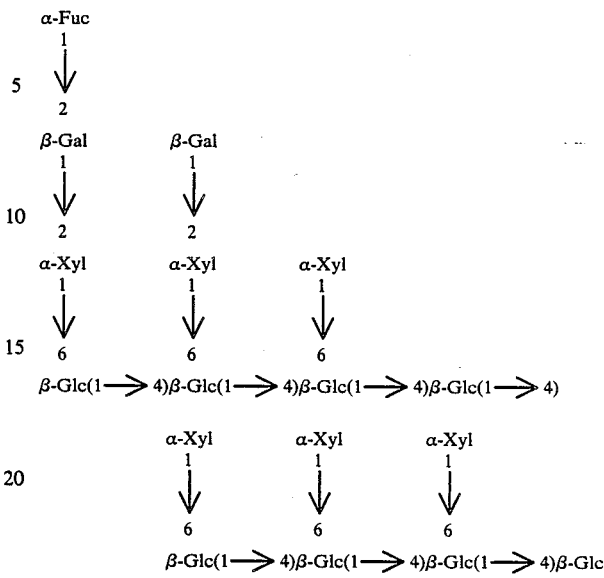

said polysaccharide fraction having immunostimulatory activity, wherein Fuc represents fucose, Gal represents galactose, Xyl represents xylose, and Glc represents glucose.

2. Biochemically pure polysaccharide fractions having an average molecular weight of about 25,000 with a molecular weight range of from about 20,000 to about 30,000 of the general structure:

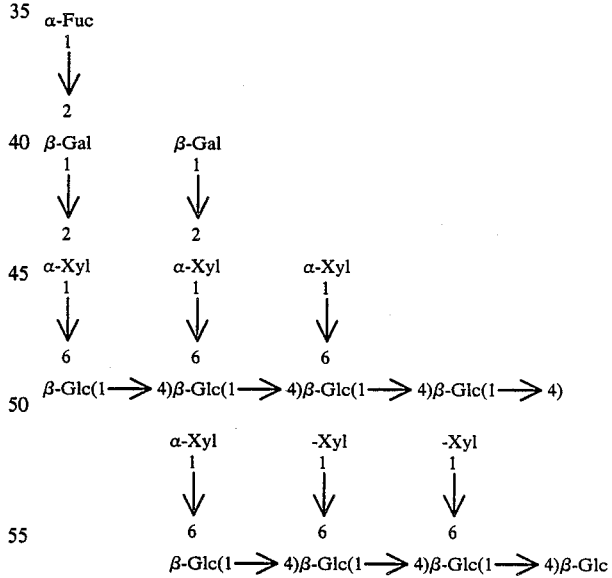

said polysaccharide fractions having immunostimulatory activity, wherein Fuc represents fucose, Gal represents galactose, Xyl represents xylose, and Glc represents glucose.

3. Biochemically pure polysaccharide fractions having an average molecular weight of about 110,000 and a molecular weight range of from about 100,000 to about 120,000 as measured in 0.2M phosphate buffer having a general structure comprising the following moieties:

(a) an arabinagalactan moiety of the formula:

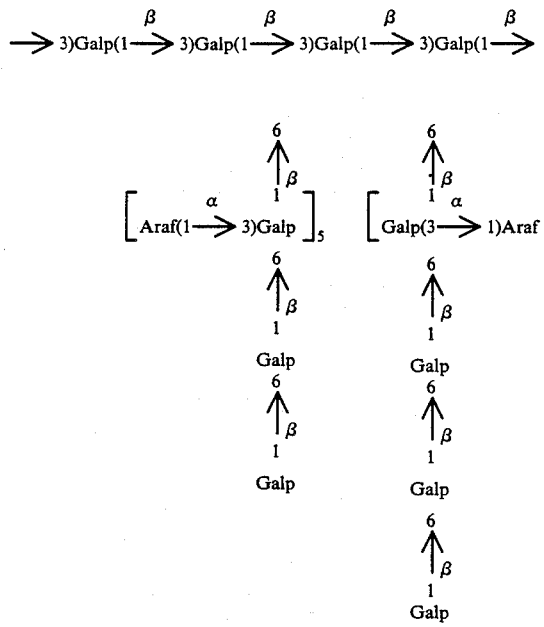

(b) a rhamnogalacturonan moiety of the formula:

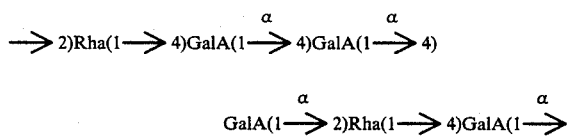

(c) an arbinan moiety of the formula:

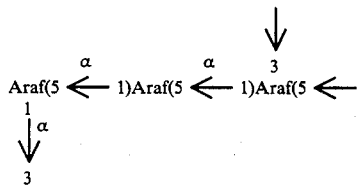

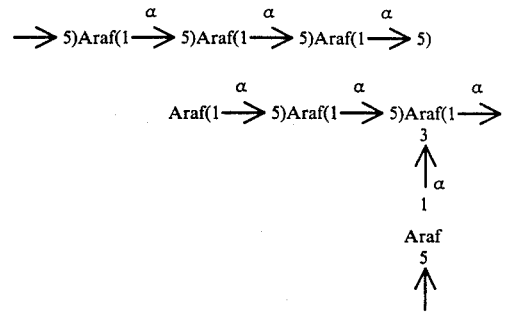

said polysaccharide fractions having immunostimulatory activity, wherein Galp represents galactopyranose, Rha represents rhamnose, GalA represents galacturonic acid and Araf represents arabinofuranose.

4. The biochemically pure polysaccharide fractions of claim 1 or claim 2 or claim 3 wherein said polysaccharides are isolated from plant cell structures of *Echinacea purpurea* (Linné) Moench or *Echinacea angustifolia* (De Vandolle).

5. A method of treating an animal requiring immune mediator comprising administering to said animal a therapeutically effective amount of the polysaccharide of claim 4.

6. A method of treating an animal requiring an immunomodulator comprising administering to said animal a therapeutically effective amount of the polysaccharide of claim 4.

7. A pharmaceutical preparation including the polysaccharide fraction of claim 1 or claim 2 or claim 3.

8. The pharmaceutical preparation of claim 7 further including a pharmaceutically acceptable vehicle.

9. A pharmaceutical preparation including the polysaccharide of claim 4.

10. The pharmaceutical preparation of claim further including a pharmaceutically acceptable vehicle.

11. The pharmaceutical preparation of claim further including at least one other pharmaceutically active compound.

* * * * *